(12) United States Patent
Sottery et al.

(10) Patent No.: US 7,193,712 B2
(45) Date of Patent: Mar. 20, 2007

(54) METHODS AND APPARATUS FOR MEASURING AN ELECTROMAGNETIC RADIATION RESPONSE PROPERTY ASSOCIATED WITH A SUBSTRATE

(75) Inventors: John Phelps Sottery, Hamden, CT (US); Mark Sekas, Orange, CT (US); Patricia Alison LaFleur, Shrewsbury, PA (US)

(73) Assignees: The Procter & Gamble Company, Cincinnati, OH (US); Innovative Measurement Solutions, Inc., Milford, CT (US)

( * ) Notice: Subject to any disclaimer, the term of this patent is extended or adjusted under 35 U.S.C. 154(b) by 0 days.

(21) Appl. No.: 10/965,240

(22) Filed: Oct. 14, 2004

(65) Prior Publication Data

US 2006/0082773 A1    Apr. 20, 2006

(51) Int. Cl.
*G01J 4/00*    (2006.01)
(52) U.S. Cl. .................................................... 356/369
(58) Field of Classification Search ............... None
See application file for complete search history.

(56) References Cited

U.S. PATENT DOCUMENTS

| | | | |
|---|---|---|---|
| 4,555,179 A * | 11/1985 | Langerholc et al. | 356/342 |
| 5,363,854 A | 11/1994 | Martens et al. | |
| 6,175,750 B1 | 1/2001 | Cook et al. | |
| 6,809,809 B2 * | 10/2004 | Kinney et al. | 356/237.5 |
| 2002/0087085 A1 | 7/2002 | Dauga et al. | |
| 2002/0095075 A1 | 7/2002 | Madarasz et al. | |
| 2003/0139672 A1 | 7/2003 | Cane et al. | |
| 2004/0008343 A1 | 1/2004 | Pawluczyk et al. | |
| 2004/0078278 A1 | 4/2004 | Dauga et al. | |
| 2004/0092802 A1 | 5/2004 | Cane et al. | |
| 2004/0169857 A1 | 9/2004 | Acosta et al. | |
| 2006/0082764 A1 | 4/2006 | Sottery et al. | |
| 2006/0085274 A1 | 4/2006 | Sottery et al | |

FOREIGN PATENT DOCUMENTS

| | | |
|---|---|---|
| WO | WO 99/05961 | 2/1999 |
| WO | WO 01/41632 A2 | 6/2001 |
| WO | WO 2004/060105 A1 | 7/2002 |
| WO | WO 03/073077 A1 | 9/2003 |

OTHER PUBLICATIONS

PCT International Search Report, dated mailed: Feb. 8, 2006, 7 pages.

* cited by examiner

*Primary Examiner*—Tu T. Nguyen
(74) *Attorney, Agent, or Firm*—Dara M. Kendall; Eric T. Addington; Vladimir Vitenberg

(57) ABSTRACT

Methods and apparatus for measuring an electromagnetic radiation response property associated with a substrate are disclosed. The methods and apparatus generate electromagnetic waves and capture a portion of the generated waves after the waves pass through a first polarized filter, reflect from a substrate, and pass through a second polarized filter arranged in a cross polar arrangement with respect to the first polarized filter. Digital data is determined from the captured electromagnetic waves. Based on the digital data, the customer is given certain choices and/or informed of certain personal care product recommendations.

20 Claims, 5 Drawing Sheets

METHODS AND APPARATUS FOR MEASURING AN ELECTROMAGNETIC RADIATION RESPONSE PROPERTY ASSOCIATED WITH A SUBSTRATE

TECHNICAL FIELD

The present invention relates in general to measurement systems and, in particular, to methods and apparatus for measuring an electromagnetic radiation response property associated with a substrate.

BACKGROUND

Countless individuals all over the world seek to improve their physical appearance through the use of personal care products such as cosmetics and skin care treatments. As a result there is an extremely large choice of available products for consumers to choose from. Often, the individual consumer finds it difficult to determine what type of products to apply and what color(s) work best for them. This problem is compounded as the individual's skin condition changes over time and/or society's norms change over time.

Beauty counselors at retail cosmetics counters are charged with assisting customers in identifying personal care products aimed at improving the customer's appearance. However, such consultations are very subjective. Not all beauty counselors identify the same type or color of personal care products. Consultation results can vary from visit to visit, even with the same counselor and client. In addition, employment of beauty counselors increases the cost of the personal care products, and many customers do not want to be inconvenienced by approaching a beauty counselor.

BRIEF DESCRIPTION OF THE DRAWINGS

Features and advantages of the disclosed methods and apparatus will be apparent to those of ordinary skill in the art in view of the detailed description of certain examples which is made with reference to the drawings, a brief description of which is provided below.

DETAILED DESCRIPTION OF EXAMPLE EMBODIMENTS

In general, the methods and apparatus described herein use an electromagnetic source, an electromagnetic capture device, and a plurality of filters in a predetermined arrangement in order to construct an apparatus for measuring an electromagnetic radiation response property associated with a substrate. A retail customer may operate the apparatus without assistance. Specifically, the customer self-aligns the substrate to be measured, e.g., a portion of his/her body, with the apparatus and triggers an electromagnetic measurement. In response, the apparatus generates electromagnetic waves and captures a portion of the generated waves after the waves pass through a first polarized filter, reflect from the customer, and pass through a second polarized filter arranged in a cross polar arrangement with respect to the first polarized filter. In addition, the apparatus captures electromagnetic waves that pass through an attenuating filter and reflect from one or more calibration standards. Digital data is determined from the captured electromagnetic waves. Based on the digital data, the customer is given certain choices and/or informed of certain recommendations, e.g., personal care product recommendations. In addition, the digital data is used to calibrate and/or recalibrate the apparatus.

Figure 1:
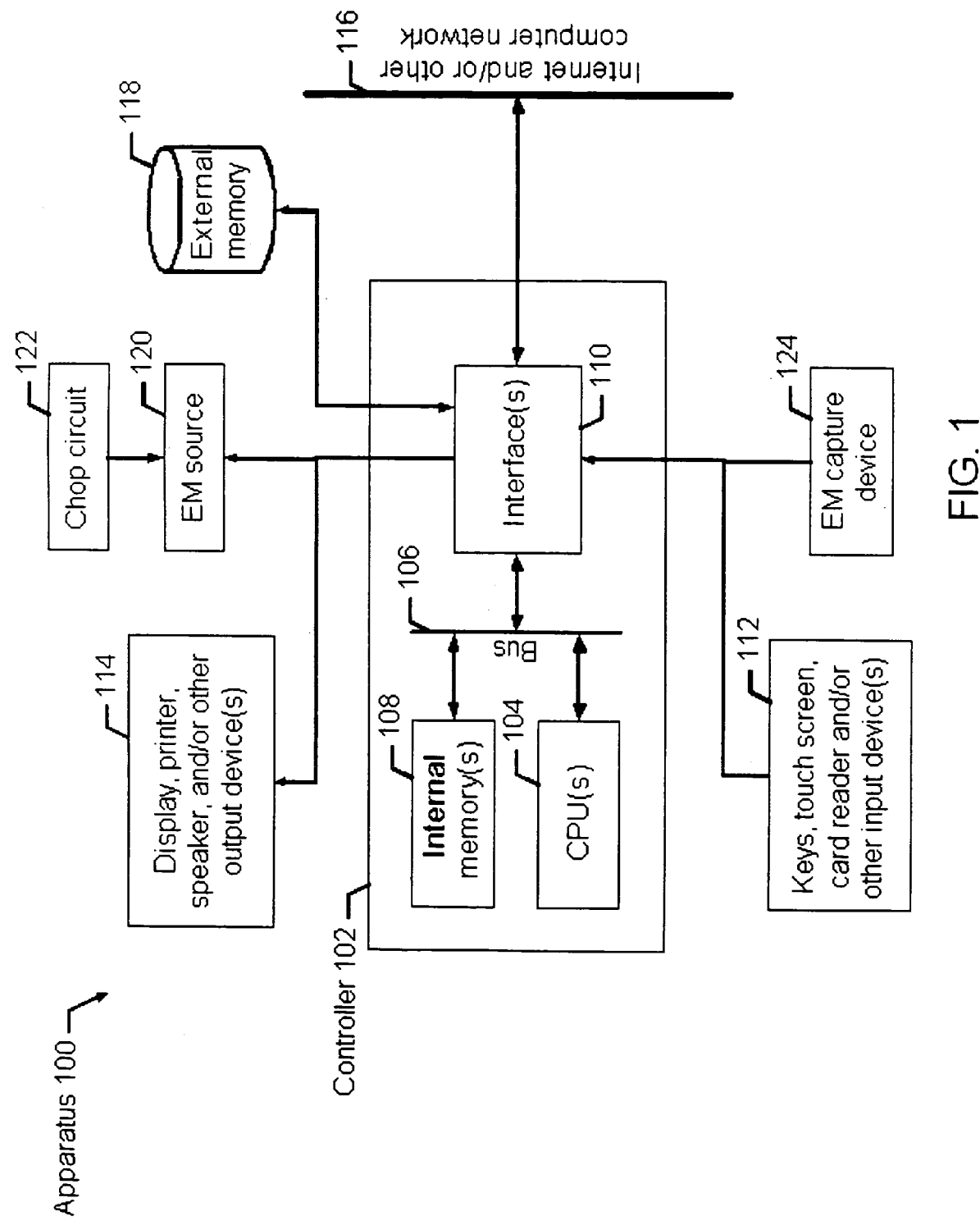
FIG. 1 is a block diagram of an apparatus structured to measure an electromagnetic radiation response property associated with a substrate.

A block diagram of an apparatus 100 structured to measure an electromagnetic radiation response property associated with a non-homogeneous/homogeneous shiny or matte substrate is illustrated in FIG. 1. The apparatus 100 includes a controller 102 which preferably includes one or more processing units 104 electrically coupled by an address/data bus 106 to one or more internal memory devices 108 and one or more interface circuits 110. Each processing unit 104 may be any type of well known microprocessor, microcontroller, digital signal processor, specialized mathematical processor, and/or any other type of computing device. The memory device(s) 108 may include volatile memory and/or nonvolatile memory. Preferably, the memory device(s) 108 store a software/firmware program that controls unit functions and interacts with a plurality of other devices as described in detail below. This program may be executed by the processing unit(s) 104 in a well known manner. The memory device(s) 108 may also store digital data indicative of screen displays, bit maps, user instructions, personal identification information, demographic data, digitized images, color data, light intensity data, histogram data, and/or other data used by the apparatus 100 and/or collected by the apparatus 100.

The interface circuit 110 may be implemented using any type of well known interface standard, such as an Ethernet interface, a Universal Serial Bus (USB) interface, and/or one or more proprietary interfaces. One or more input devices 112 may be connected to the interface circuit 110 for entering data, signals, user identification information, commands, and/or other information into the controller 102. For example, the input device 112 may be one or more keys, one or more buttons, a touch screen, a card reader and/or other input device(s).

One or more displays, printers, speakers, and/or other output devices 114 may also be connected to the controller 102 via the interface circuit 110. The display 114 may be cathode ray tube (CRTs), liquid crystal displays (LCDs), or any other type of display. The display 114 may generate visual displays of data generated and/or retrieved during operation of the apparatus 100. The visual displays may include prompts for human input, calculated values, detected data, etc. The display 114 is typically used to display instructions and product recommendations to a user. For example, the visual displays may instruct a retail customer how to self-align using a pair of eye positioning frames and trigger a measurement by pushing a button 112. In addition, the instructions may request certain consumer data and/or personal identification information. Still further, the display may inform a customer of a particular product name and/or color.

The apparatus 100 may also exchange data with other devices via a connection to a network 116. The network connection may be any type of network connection. For example, the network connection may be, but is not limited to, an Ethernet connection, digital subscriber line (DSL), telephone line, or coaxial cable. Of course, a person of ordinary skill in the art will readily appreciate that any type of data communication, such as a direct connection, may be used. Users of the apparatus 100 may be asked to register. In such an instance, each user may choose a user identifier and a password that may be required for the activation of services. The user identifier and/or password may be entered into the apparatus 100 via a card reader and/or other input device 112.

The apparatus 100 may also include one or more external memory devices 118. For example, the apparatus 100 may include one or more flash card readers, hard drives, a compact disk (CD) drive, a digital versatile disk drive (DVD), and/or other computer media input/output (I/O) devices.

The apparatus 100 also includes an electromagnetic (EM) capture device 124 which may also include a shutter mechanism to control the time the electromagnetic capture device is exposed to the electromagnetic signal. The electromagnetic capture device 124 produces an electrical signal in response to an electromagnetic signal. The electromagnetic capture device 124 "captures" electromagnetic waves, such as light waves, infrared waves, and/or ultraviolet waves. In order to produce a certain type of electromagnetic wave, the electromagnetic source 120 may include one or more filters, such as infrared, ultraviolet, visible light, chop and/or band pass. In one example, the electromagnetic source 120 produces a pulse of electromagnetic energy using a flash, such as a xenon flash lamp, a linear flash and/or a ring flash. In another example, the electromagnetic source 120 is a continuous source.

The apparatus 100 may also include a chop circuit 122, such as a thyristor chop circuit.

The chop circuit 122 cuts off the electromagnetic source 120 when a predetermined amount of electromagnetic radiation is detected. The chop circuit 122 may be connected to the electromagnetic source 120 directly (as shown) or indirectly via the controller 102.

The apparatus 100 also includes an electromagnetic (EM) capture device 124. The electromagnetic capture device 124 captures electromagnetic waves, such as light waves, infrared waves, and/or ultraviolet waves. Preferably, the captured waves are represented by a digital value indicative of light intensity. For example, three digital values may be used to represent the light intensity in each of a red, a green, and a blue color spectrum. In such an instance, the electromagnetic capture device 124 may include color filters corresponding to the represented wavelength regions. Of course, a person of ordinary skill in the art will readily appreciate that any band of wavelength may be represented, such as a yellow band, an infrared band, and/or an ultraviolet band. The electromagnetic capture device 124 may be any type of well known electromagnetic capture device. For example, the electromagnetic capture device 124 may be a charge coupled device (CCD), a CMOS device, and/or a linear photo diode array.

Figure 2:
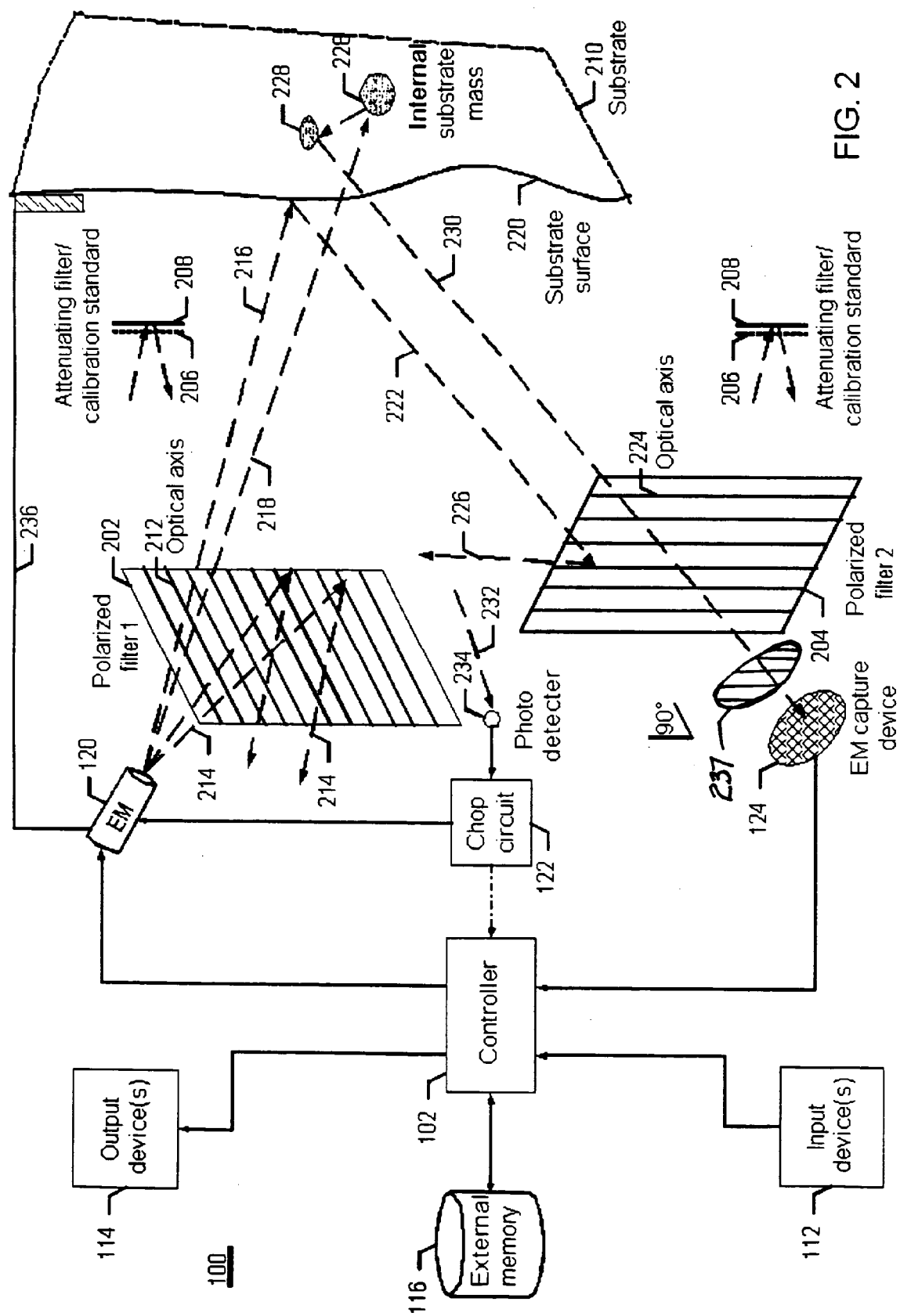
FIG. 2 is a more detailed block diagram of the apparatus illustrated in FIG. 1.

A block diagram of the apparatus 100 with additional details shown is illustrated in FIG. 2. Specifically, a first polarized filter 202, a second polarized filter 204, an attenuating filter 206, one or more calibration standards 208 and a lens 237 are shown. The first polarized filter 202 may be located between the electromagnetic source 120 and a substrate 210. The second polarized filter 204 may be located between the substrate 210 and the electromagnetic capture device 124. The lens 237 may be located between the second polarized filter 204 and the electromagnetic capture device 124.

The lens 237 may be any material (glass, quartz, plastic, fused silica) that allows electromagnetic radiation of specific wavelengths to pass through, and may also include an adjustable or fixed aperture to attenuate the electromagnetic radiation. The first polarized filter 202 may be any type of material that only allows light with a specific plane or polarization to pass through. The direction of fluctuation passed by a polarized filter is often called the "easy" axis or the "optical" axis. The first polarized filter 202 is arranged such that the optical axis 212 associated with the first polarized filter 202 is aligned in a predetermined direction. For example, the first polarized filter 202 may be arranged such that the optical axis 212 associated with the first polarized filter 202 is aligned horizontally with respect to the floor of an installation site or retail point of sale. Accordingly, some electromagnetic waves 214 emanating from the electromagnetic source 120 may be absorbed and/or reflected by the first polarized filter 202. In other words, all (or almost all) of the electromagnetic waves 216, 218 passing through the first polarized filter 202 will be linearly polarized in a first direction dictated by the optical axis 212 of the first polarized filter 202.

The substrate 210 may be any material. Preferably, the substrate 210 is a portion of a human body. For example, the substrate 210 may be a portion of a human face, a human tooth, human hair, a human chest, a human neck, a human arm, a human hand, and/or a human leg. A substrate surface 220 reflects some of the electromagnetic waves 222 generated by the electromagnetic source 120. Typically, a significant fraction of these reflected electromagnetic waves 222 are linearly polarized in the same plane as the incident electromagnetic waves 216 (i.e., for waves specularly reflected from a surface, polarization is maintained). In other words, many of the reflected waves 222 are linearly polarized in a direction dictated by the optical axis 212 of the first polarized filter 202.

The second polarized filter 204 may also be any type of material that only allows light with a specific plane of polarization to pass through. The second polarized filter 204 is preferably arranged such that the optical axis 224 associated with the second polarized filter 204 is non-parallel with respect to the optical axis 212 associated with the first polarized filter 202 (i.e., forming a non-zero angle). For example, the second polarized filter 204 may be arranged such that the optical axis 224 associated with the second polarized filter 204 is nearly perpendicular (e.g., forming an angle between 70 and 110 degrees) or substantially perpendicular (e.g., forming an angle between 85 and 95 degrees) to the optical axis 212 associated with the first polarized filter 202. Accordingly, reflected waves 222 which are linearly polarized in a direction dictated by the optical axis 212 of the first polarized filter 202 may be further absorbed and/or reflected 226 by the second polarized filter 204. In other words, a large percentage of the electromagnetic waves which are generated by the electromagnetic source 120 and reflected by the substrate surface 212 are blocked by the second polarized filter 204 and do not arrive at the electromagnetic capture device 124.

Concurrently, some of the electromagnetic waves 218, which are generated by the electromagnetic source 120 and pass through the first polarized filter 202, start out to be linearly polarized in a first direction dictated by the optical axis 212 of the first polarized filter 202. However, some fraction of these electromagnetic waves 218 penetrate through the substrate surface 220 and undergo one or more scattering events against internal substrate masses 228. In such an instance, some fraction of the incident electromagnetic waves 218 may emerge from the substrate 210 as a wave 230 with a different polarization. Some fraction of the emergent wave 230 may be linearly polarized (in whole or in part) in a second direction consistent with the optical axis 224 of the second polarized filter 204. Accordingly, such an electromagnetic wave 230 passes through the second polarized filter 204 with minimum attenuation, passes through the lens 237 and arrives at the electromagnetic capture device 124. In this manner, much of the "surface reflection" is eliminated from the electromagnetic measurement, while a significant portion of the remitted electromagnetic waves (i.e., waves that have undergone one or more scattering events with internal substrate mass) are used in the electromagnetic measurement. In this manner, the system effectively discriminates against electromagnetic waves that reflect off the substrate surface (polarization maintained) and preferentially measures the (depolarized) electromagnetic waves that are remitted from the substrate after one or more collisions with internal substrate masses.

Furthermore, background electromagnetic radiation (electromagnetic radiation that is present in the environment and not produced by the apparatus 100) can adversely affect the measurement of the substrate. Thus the variables that impact the response of the system to background electromagnetic radiation including the lens, lens aperture, transmittance of the polarizing filters, period of time the electromagnetic radiation is allowed to strike the electromagnetic capture device and the inherent sensitivity/integration time of the electromagnetic capture device need to be selected such that the electromagnetic capture device does not yield an appreciable signal from the background electromagnetic radiation. For example, in one preferred embodiment, a lens aperture of F8 coupled with 38% transmission polarizing filters, an exposure time of 2 milliseconds and a CMOS inherent sensitivity/integration time equivalent to ISO 100 yielded no appreciable signal for background electromagnetic radiation.

One or more attenuating filters 206 and one or more calibration standards 208 may be used to calibrate the apparatus each time a substrate measurement is taken. The calibration standards may be any type of material, such as a blend of pigments fixed in a polymer and/or protein matrix. Preferably, the calibration standards 208 reflect the electromagnetic waves generated by the electromagnetic source 120 in a manner that is similar to the way the substrate 210 reflects the electromagnetic waves generated by the electromagnetic source 120. For example, one calibration standard 208 may reflect one color that is typical for the substrate 210 being tested (e.g., light skin color, yellow skin color, etc.), and another calibration standard 208 may reflect another color that is typical for the substrate 210 being tested (e.g., dark skin color, red skin color, etc.). Each of these colors is associated with a known digital value. As a result, digital values obtained from measuring unknown substrates 210 may be compared to these known values each time a measurement is taken in order to ensure calibration in a cost-effective manner.

However, in one embodiment, the calibration standards 208 are located in a different plane than the substrate 210. Preferably, the standards 208 and the substrate 210 are protected from environmental damage by one or more housings. For example, the calibration standards 208 may be located a first distance from the electromagnetic source 120, and the substrate 210 may be located a second distance from the electromagnetic source 120, wherein the first distance is shorter than the second distance (i.e., the calibration standards 208 may be closer to the electromagnetic source 120 than the substrate 210). As a result, the calibration standards 208 receive more electromagnetic energy per unit area than the more distant substrate 210. In such an instance, an attenuating filter 206 may be placed between the electromagnetic source 120 and the calibration standards 208 in order to attenuate the amount of electromagnetic energy reaching the calibration standards 208. Preferably, the percentage of attenuation associated with the attenuating filter 206 is based on a function of the ratio of the first distance (i.e., distance from electromagnetic source 120 to calibration standards 208) and the second distance (i.e., distance from electromagnetic source 120 to substrate 210).

Figure 3A:
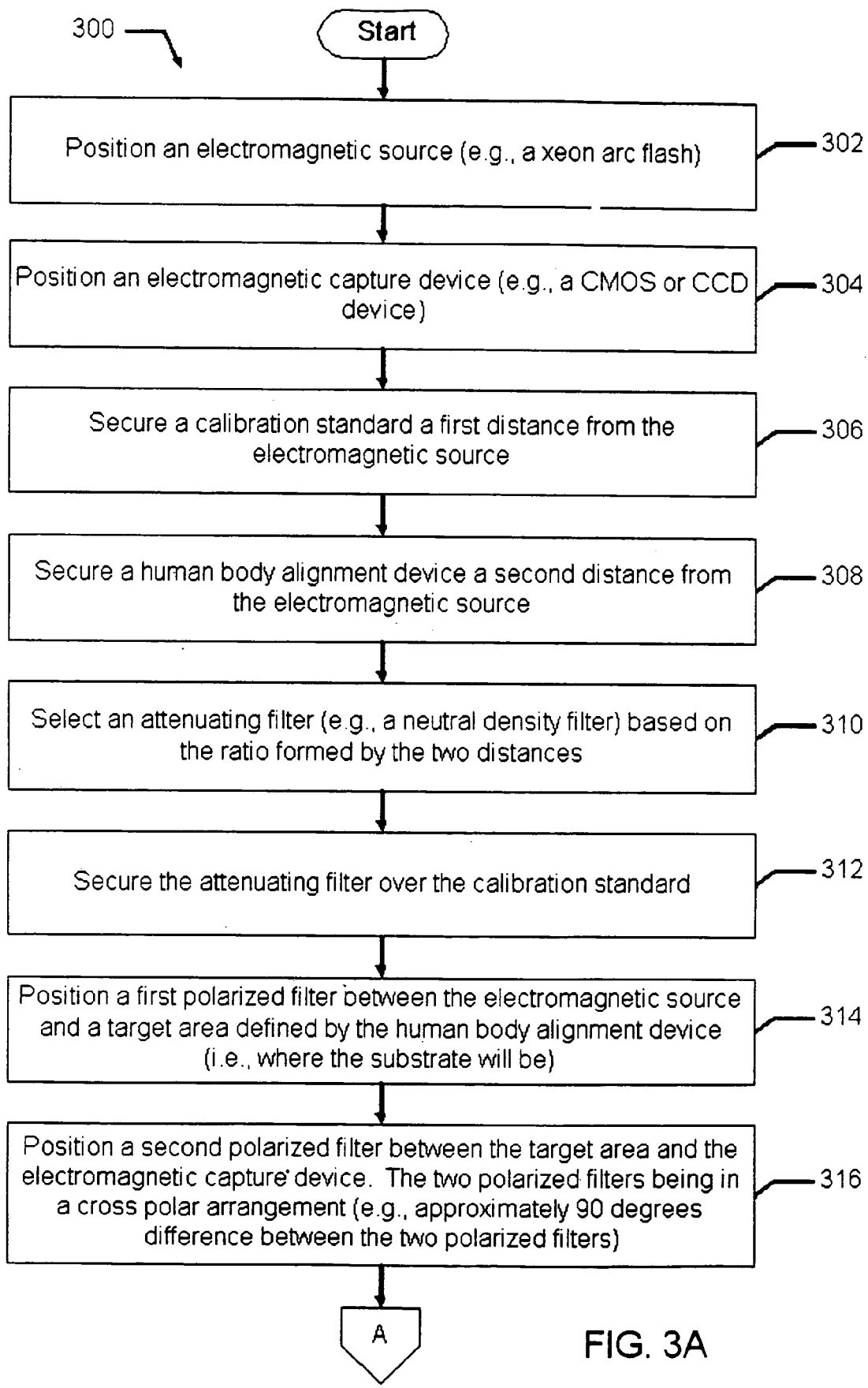
FIGS. 3A–3C is a flowchart of a process for measuring an electromagnetic radiation response property associated with a substrate.
Figure 3B:
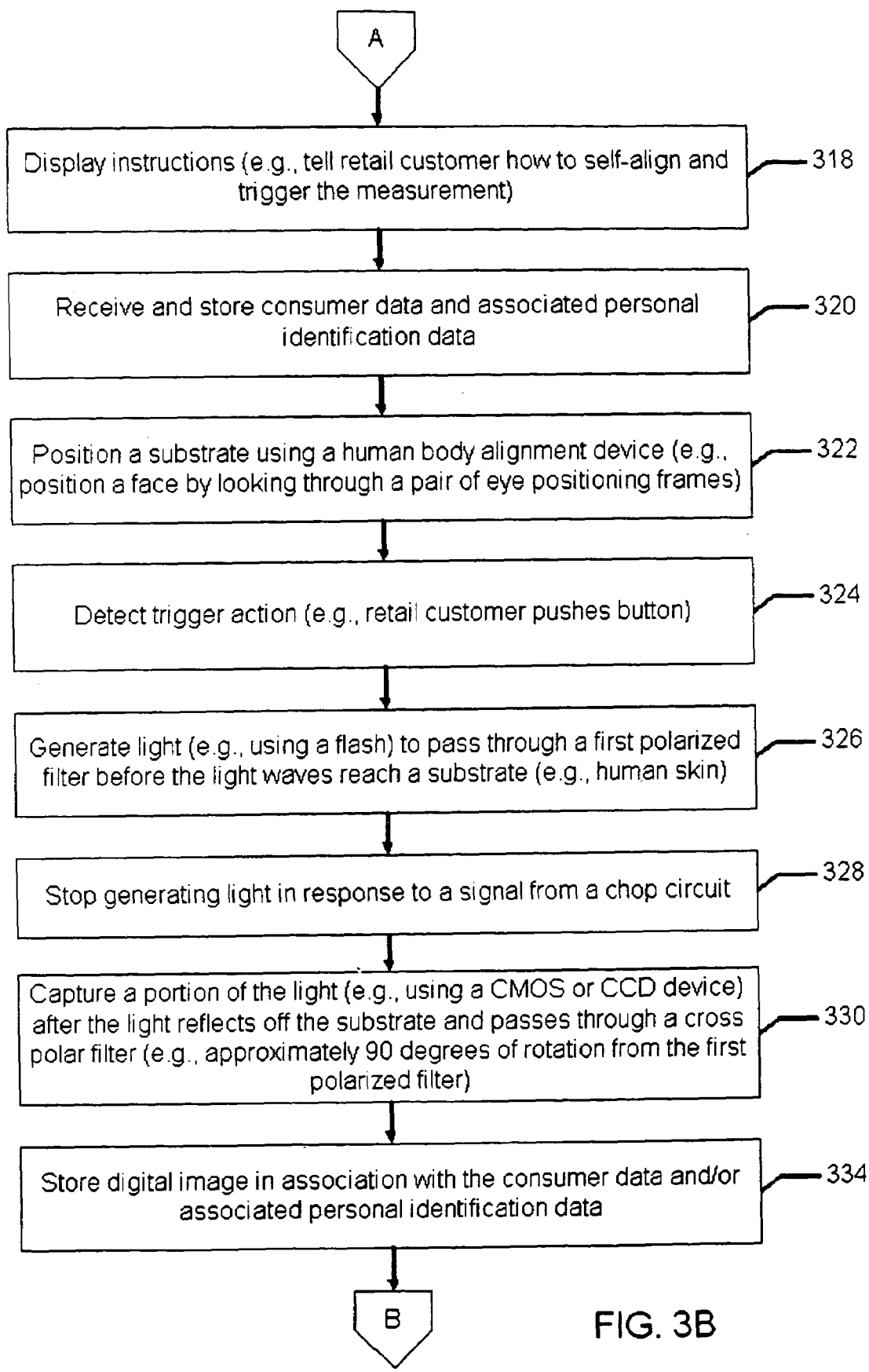
Figure 3C:
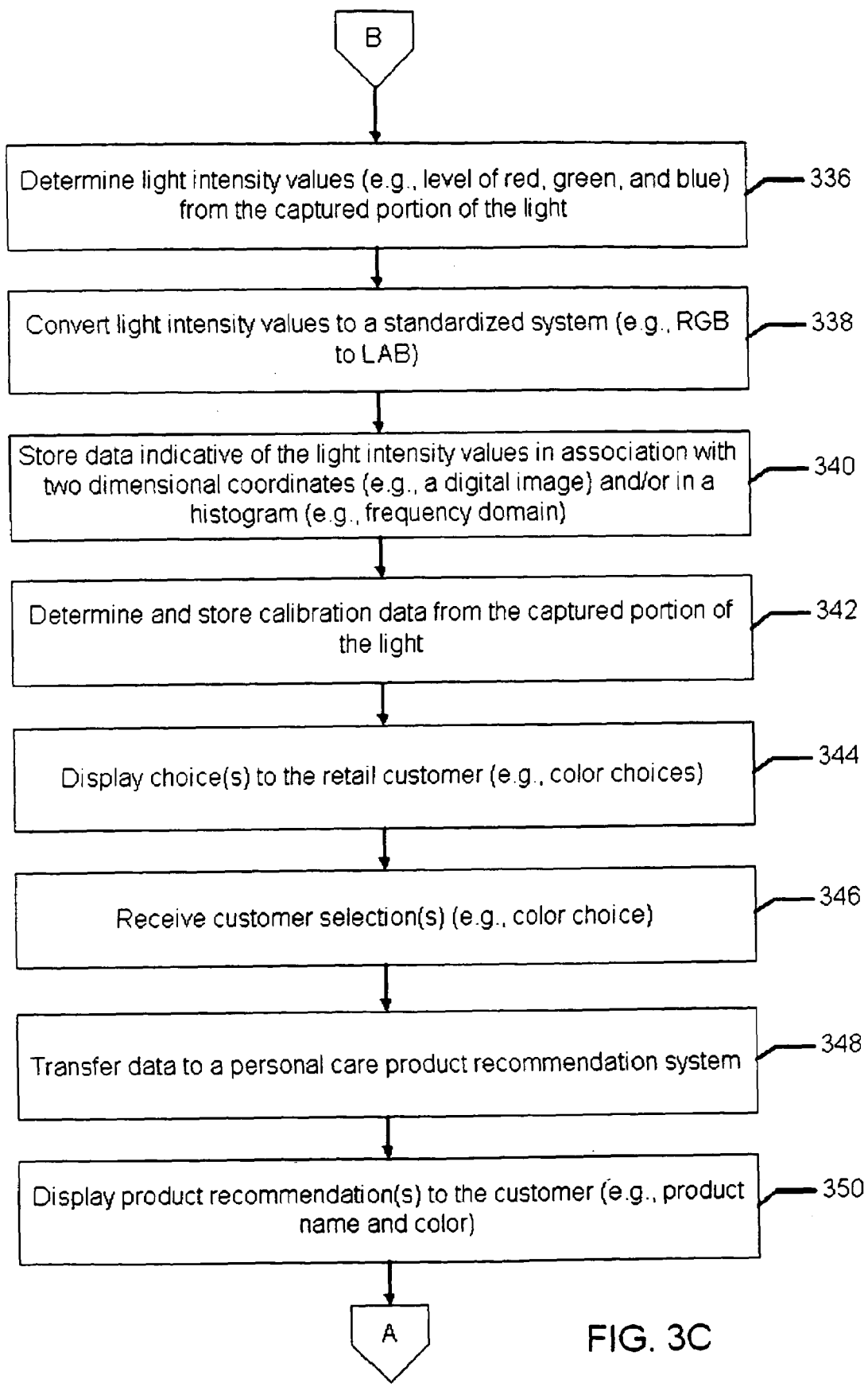

A flowchart of a process 300 for measuring an electromagnetic radiation response property associated with a substrate is illustrated in FIG. 3. Preferably, part of the process 300 is embodied in a software program that is stored in a controller memory 108, 118 and executed by the controller processing unit 104 in a well known manner. However, some of the steps of the process 300 may be performed manually and/or by another device. Although the process 300 is described with reference to the flowchart illustrated in FIG. 3, a person of ordinary skill in the art will readily appreciate that many other methods of performing the acts associated with process 300 may be used. For example, the order of many of the steps may be changed. In addition, many of the steps described are optional.

Generally, the process 300 positions an electromagnetic source 120, an electromagnetic capture device 124, and a plurality of filters 202, 204, 206 in a predetermined arrangement in order to construct an apparatus 100 for measuring an electromagnetic radiation response property associated with a substrate 210. A retail customer may operate the apparatus without assistance. Specifically, the customer self-aligns a portion of his/her body with the apparatus 100 and triggers an electromagnetic measurement. In response, the apparatus 100 generates electromagnetic waves and captures a portion of the generated waves after the waves pass through a first polarized filter 202, reflect from the customer (i.e., the substrate 210 and/or the substrate surface 220), pass through a second polarized filter 204 arranged in a cross polar arrangement with respect to the first polarized filter 202 and pass through the lens 237. In addition, the apparatus 100 captures electromagnetic waves that pass through an optional attenuating filter 206 and reflect from one or more calibration standards 208. Digital data is determined from the captured electromagnetic waves. Based on the digital data, the customer is given certain choices and/or informed of certain personal care product recommendations. In addition, the digital data may be used to calibrate/recalibrate the apparatus.

The process 300 begins when an electromagnetic source 120 is placed in a predetermined position (block 302). For example, a xenon flash lamp may be fixed to a housing and/or the housing may be fixed to a structure at a retail point of sale. Similarly, an electromagnetic capture device 124 is placed in a predetermined position relative to the electromagnetic source 120 (block 304). For example, a charge coupled device, a CMOS device, and/or a linear photo diode array may be placed in approximately the same location as the electromagnetic capture device. In addition, one or more calibration standards 208 may be secured a first predetermined distance from the electromagnetic source 120 (block 306). For example, several different color standards may be placed inside the housing of the apparatus 100. Similarly, a human body alignment device 236 is secured a second distance from the electromagnetic source 120 (block 308).

Once these two distances are determined, an attenuating filter 206 may be selected based on the function of the ratio formed by the two distances (block 310). For example, a neutral density filter that attenuates light or other electromagnet waves by a certain percentage (e.g., absorbance between 0.1 and 3.0) may be selected based on the ratio. Larger ratios of the second distance over the first distance indicate a larger amount of attenuation should be used in order to simulate an arrangement where the calibration standards 208 are in approximately the same plane as the substrate 210. Once the attenuating filter 206 is selected, the attenuating filter 206 may be secured over the calibration standards 208 (block 312).

In addition, a first polarized filter is positioned between the electromagnetic source 120 and a target area defined by the human body alignment device 236 (block 314). The human body alignment device 236 defines approximately where the substrate 210 will be positioned during a measurement by the apparatus 100. The human body alignment device 236 may be any type of alignment device, such as a pair of eye positioning frames. Eye positioning frames may be used to position a human head for measurement of any portion of the human head, such as hair, teeth, face, neck, etc.

Similarly, a second polarized filter is positioned between the target area (as defined by the human body alignment device 236) and the electromagnetic capture device 124 (block 316). The two polarized filters are placed in a cross polar arrangement. In other words, the optical axis 212 of the first polarized filter is not parallel to the optical axis 224 of the second polarized filter. Preferably, the two optical axes 212, 224 are separated by approximately ninety degrees.

A lens 237 is optionally placed between the second polarized filter 204 and the electromagnetic capture device 124. Once the measurement apparatus 100 is constructed, the apparatus preferably displays instructions on an output device 114 (block 318). Preferably, the instructions are indicative of a procedure, at least a portion of which the retail customer is to perform without retail employee assistance. The procedure facilitates alignment of the retail customer with the apparatus 100 using the human body alignment device 236. In addition, the instructions preferably include an action the retail customer is to perform in order to trigger an electromagnetic measurement by the apparatus 100. For example, the instructions may tell a retail customer how to self-align using a pair of eye positioning frames and trigger a measurement by pushing a button 112. In addition, the instructions may request certain consumer data and/or personal identification information. In such an instance, the apparatus 100 receives the consumer data and/or personal identification information via one or more input devices 112 and stores the consumer data and/or personal identification information in a memory 108, 118 (block 320). For example, the apparatus 100 may receive personal identification information via a personal identification device such as a card reader and/or a touch screen device. Subsequently, the substrate 210 is positioned using the human body alignment device 236 (block 322). For example, a pair of eye positioning frames may be used to position a human face for measurement.

Once the trigger action is detected (block 324), the apparatus 100 generates electromagnetic radiation (block 326). For example, a retail customer being measured may self-align using the eye positioning frames and push a button to trigger the measurement. In response, the apparatus 100 may trigger a flash, such as a xenon flash. Of course, a person of ordinary skill in the art will readily appreciate that a continuous light source or any electromagnetic source may be used. For example, an infrared and/or an ultraviolet source may be used. Some of the electromagnetic waves 216, 218 generated by the electromagnetic source 120 then pass through the first polarized filter 202 before the waves reach the substrate 210. Other electromagnetic waves 214 generated by the electromagnetic source 120 do not pass through the first polarized filter 202. Instead, these waves 214 are absorbed and/or reflected by the first polarized filter 202. As a result, the electromagnetic waves 216, 218 passing through the first polarized filter 202 are linearly polarized in a first direction dictated by the optical axis 212 of the first polarized filter 202.

Some of the electromagnetic waves 232 that pass through the first polarized filter 202 reflect from the substrate 210 and strike a photo detector 234 which is part of a chop circuit 122. If a predetermined amount of electromagnetic radiation reaches the detector 234, the chop circuit 122 preferably cuts off the electromagnetic source 120 (block 328). In this manner, insufficient lighting and/or saturation of the electromagnetic capture device 124 is avoided. For example, a "light" substrate preferably causes the chop circuit 122 to trigger earlier than a "dark" substrate. In conjunction with the calibration standards, this technique allows a greater dynamic range of substrate shades to be accurately measured (e.g., from very light to very dark).

Some of the electromagnetic waves 216, 222, 226 that pass through the first polarized filter 202 reflect from the substrate surface 220 and are absorbed and/or reflected by the second polarized filter 204. However, some of the electromagnetic waves 218, 230 that pass through the first polarized filter 202 reflect from internal substrate masses 228, pass through the second polarized filter 204 and the lens 237. These waves 218, 230 are captured by the electromagnetic capture device 124 (block 330). Different waves captured by the electromagnetic capture device 124 at different X-Y coordinates of the electromagnetic capture device 124 may be stored separately in a two-dimensional data matrix (block 334). This two-dimensional matrix may be stored in conjunction with the consumer data and/or the personal identification data associated with this retail customer (block 334).

The light intensity values may be converted from the original color space to any other color space (block 338) prior to or after creating a histogram. For example, the light intensity value may be converted from a RGB (red-green-blue) system to a LAB (light-yellow-red) and/or a LCH (light-chroma-hue) system. Digital representations of the different waves or converted versions thereof captured at the different X-Y coordinates of the electromagnetic capture device 124 may be combined in to a histogram by determining the light intensity values associated with each of the different X-Y coordinates and counting the number of occurrences of each light intensity value (or each of a range of light intensity values) (block 336). One or more of the above combinations of data is stored in an apparatus memory 108, 118 (block 340).

As discussed above, one or more calibration standards 208 reflect the electromagnetic waves generated by the electromagnetic source 120 in a manner that is similar to the way the substrate 210 and/or substrate surface 220 reflects the electromagnetic waves generated by the electromagnetic source 120. Each calibration standard 208 is associated with a known digital value. Accordingly, digital data indicative of electromagnetic radiation intensities captured by the electromagnetic capture device 124 in areas where calibration standards 208 are known to be located may be stored in an apparatus memory 108, 118 and used to calibrate the apparatus 100 for the current and/or subsequent measurements (block 342).

In one example use of the apparatus 100, the retail customer may need to make a color choice decision. For example, if the apparatus 100 is being used in conjunction with a hair color product recommendation system, and the customer's hair color analysis results in a bimodal distribution (i.e., primarily two colors are present), the apparatus 100 may ask the customer to choose one of the two colors as the preferred color. Accordingly, the apparatus 100 may display the two choices on an output device 114 (block 344) and receive a selection from the customer (block 346). For example, the apparatus 100 may display two polygon areas of color on a touch sensitive display 114 which may be touched to indicate a selection.

Regardless of whether a selection by the consumer is requested, the apparatus 100 may transfer data indicative of the measurement to a personal care product recommendation system (block 348). The personal care product recommendation system may be implemented in software and executed by the controller 102. When the personal care product recommendation system determines one or more recommend products and/or services, those products and/or service may be displayed to the retail customer via an output device 114 (block 350). For example, the apparatus may display a product name and/or a color.

In summary, persons of ordinary skill in the art will readily appreciate that methods and apparatus for measuring an electromagnetic radiation response property associated with a substrate have been provided. The foregoing description has been presented for the purposes of illustration and description. It is not intended to be exhaustive or to limit the invention to the example embodiments disclosed. Many modifications and variations are possible in light of the above teachings. It is intended that the scope of the invention not be limited by this detailed description of example embodiments, but rather by the claims appended hereto.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of measuring an electromagnetic radiation response property associated with a substrate, the method comprising:
   producing electromagnetic waves which pass through a first polarized filter before the electromagnetic waves reach the substrate, the first polarized filter having a first optical axis;
   capturing a portion of the electromagnetic waves after the portion of the electromagnetic waves reflect off the substrate and pass through a second polarized filter, the second polarized filter having a second optical axis, the first optical axis being non-parallel with the second optical axis;
   determining a first light intensity value associated with a first coordinate of the substrate from the captured portion of the electromagnetic waves;
   determining a second light intensity value associated with a second coordinate of the substrate from the captured portion of the electromagnetic waves, the second light intensity value being different than the first light intensity value, the second coordinate being different than the first coordinate; and
   storing a representation of the first light intensity value and the second light intensity value in an electronic storage device;
   wherein introducing electromagnetic waves comprises termination of a light pulse by a chop circuit, wherein the chop circuit terminates in response to a detection of a predetermined amount of electromagnetic radiation reflected from the substrate.

2. A method as defined in claim 1, further comprising:
   determining that a first plurality of coordinates fall within a first predetermined range of light intensity values, the first plurality of coordinates including the first light intensity value;
   determining a first number of coordinates in the first plurality of coordinates;
   determining that a second plurality of coordinates fall within a second predetermined range of light intensity values, the second plurality of coordinates including the second light intensity value;
   determining a second number of coordinates in the second plurality of coordinates; and
   storing the first number and the second number in the electronic storage device.

3. A method as defined in claim 2, wherein storing the first number and the second number in the electronic storage device comprises storing the first number and the second number in a histogram.

4. A method as defined in claim 1, wherein producing electromagnetic waves comprises producing a light pulse from a flash lamp, the flash lamp being associated with a filter selected from the group consisting of a ultraviolet band pass filter an infrared band pass filter, a visible light band pass filter., and combinations thereof.

5. A method as defined in claim 1, wherein producing electromagnetic waves comprises activating a xenon flash lamp.

6. A method as defined in claim 1, wherein producing electromagnetic waves comprises activating a ring flash.

7. A method as defined in claim 1, wherein producing electromagnetic waves comprises activating at least two flashes.

8. A method as defined in claim 1, wherein capturing a portion of the electromagnetic waves comprises receiving the portion of the electromagnetic waves by at least one of a charge coupled device, a CMOS device, and a linear photo diode array.

9. A method as defined in claim 1, wherein an angle defined by the first optical axis and the second optical axis is between 70 and 110 degrees.

10. A method as defined in claim 1, further comprising determining a red component and a yellow component associated with the first light intensity value.

11. A method as defined in claim 1, further comprising determining a red component, a green component, and a blue component associated with the first light intensity value.

12. A method as defined in claim 1, further comprising converting an RGB value to an LAB value.

13. A method as defined in claim 1, wherein storing a representation of the first light intensity value and the second light intensity value in an electronic storage device comprises storing a digitized value in a computer memory device.

14. A method as defined in claim 1, further comprising positioning a portion of a human body in a predefined position using a human body alignment device.

15. A method as defined in claim 1, further comprising storing a plurality of two-dimensional data matrices.

16. A method as defined in claim 15, further comprising storing a plurality of consumer data associated with the two-dimensional data matrices.

17. A method as defined in claim 16, further comprising receiving personal identification data and associating the personal identification data with the plurality of consumer data.

18. A method as defined in claim 17, wherein receiving personal identification data comprises reading a personal identification device.

19. A method as defined in claim 1, further comprising recalibrating the first light intensity value and second light intensity value based on capturing a portion of the electromagnetic waves from a standard first light intensity value and a standard second light intensity value.

20. A computer readable medium storing a software program, the software program being structured to cause an apparatus to:

produce electromagnetic waves which passes through a first polarized filter before the electromagnetic waves reaches a substrate, the first polarized filter having a first optical axis;

capture a portion of the electromagnetic waves after the portion of the electromagnetic waves reflect off the substrate and pass through a second polarized filter, the second polarized filter having a second optical axis, the first optical axis being non-parallel with the second optical axis;

determine a first coordinate and a first electromagnetic value associated with the first coordinate from the captured portion of the electromagnetic waves;

determine a second coordinate and a second electromagnetic value associated with the second coordinate from the captured portion of the electromagnetic waves, the second coordinate being different than the first coordinate;

store a representation of the first coordinate, the first electromagnetic value, the second coordinate, and the second electromagnetic value in an electronic storage device; and terminate production of the electromagnetic waves by a chop circuit, wherein the chop circuit terminates in response to a detection of a predetermined amount of electromagnetic radiation reflected from the substrate.

* * * * *